US00PP24953P3

(12) United States Plant Patent
Cosner et al.

(10) Patent No.: US PP24,953 P3
(45) Date of Patent: Oct. 7, 2014

(54) *LOTUS* VINE NAMED 'COFLASH'

(50) Latin Name: ***Lotus* hybrid**
Varietal Denomination: CoFlash

(76) Inventors: Harlan B. Cosner, Rogue River, OR (US); Susan L. Cosner, Rogue River, OR (US)

( * ) Notice: Subject to any disclaimer, the term of this patent is extended or adjusted under 35 U.S.C. 154(b) by 185 days.

(21) Appl. No.: 13/506,139

(22) Filed: Mar. 28, 2012

(65) Prior Publication Data

US 2013/0263344 P1 Oct. 3, 2013

(51) Int. Cl.
*A01H 5/00* (2006.01)

(52) U.S. Cl.
USPC ..... Plt./226

(58) Field of Classification Search
USPC ..... Plt./226
See application file for complete search history.

(56) References Cited

U.S. PATENT DOCUMENTS

PP10,864 P * 4/1999 Cosner et al. ..... Plt./226
PP10,868 P * 4/1999 Cosner et al. ..... Plt./226
PP14,118 P3 * 9/2003 Cosner ..... Plt./226

* cited by examiner

*Primary Examiner* — Wendy C Haas

(57) ABSTRACT

A new and distinct cultivar of *Lotus* hybrid plant named 'CoFlash', characterized by its pendulous growth habit and pan-seasonal production of yellow-red flowers.

2 Drawing Sheets

BACKGROUND OF THE INVENTION

1. Field of Invention

The present invention relates to a new and distinct cultivar botanically known as *Lotus* hybrid, and hereinafter referred to by the cultivar name 'CoFlash'.

The cultivar of the accompanying photograph was developed and selected in a controlled breeding program in Rogue River, Oreg., by the inventor, Harlan Cosner and Susan Cosner, as described herein.

The plant is intended primarily to be ornamentally used in, for example, hanging baskets, in colder regions of the United States, and possibly as ground cover in regions of warmer winters, with minimum temperatures above 25° F.

2. Description of the Relevant Art

'CoFlash' is a result of a cross between a *Lotus* hybrid and a *Lotus maculata*. The pollen parent was 'Amazon Sunset' (U.S. Plant Pat. No. 10,864). The seed parent was 'TiGo' (U.S. Plant Pat. No. 14,118.).

The seed parent was of similar color, but was far less floriferous, producing at least 30% less flowers. Flowering may also decrease in possible photoperiodic reaction to winter short dull days.

The primary difference between the pollen parent and the instant plant is in flower color, the flowers of the instant plant appear yellow with a red tinge when observed at a distance of a few feet while the flowers of the pollen parent appear scarlet or red.

The plant was discovered as a seedling from a controlled cross-pollination made by the inventor under greenhouse conditions. The plant was produced in a controlled breeding program at Rogue River, Oreg. First asexual production was completed in Rogue River, Oreg. at least as early as Aug. 5, 2008.

Asexual propagation of the cultivar by lateral or apical stems with leaves has proven the plant to be stable in successive generations.

Color references are according to The Royal Horticultural Society Colour Chart 2011 edition, except where general terms of ordinary dictionary significance are used.

SUMMARY OF THE INVENTION

A new and distinct cultivar of *Lotus* hybrid having a pendulous plant habit and pan-seasonal production of yellow-red bi-color flowers, which appear yellow from a distance of a few feet.

DESCRIPTION OF THE PHOTOGRAPHS

The attached color photographs illustrate the cultivar of the present invention at first inflorescense.

The first photograph depicts a hanging basket of the cultivar at first inflorescense.

The second photograph depicts a close-up of the flowers of the cultivar.

PLANT DESCRIPTION

The following observations, measurements and description of the plant and flowers are based on the following environment and cultural practices at Rogue River, Oreg. The following measurements, values and comparisons describe plants grown under a double layer of polyethylene film with temperatures ranging from between 60° F. to 68° F. at night, and between 85° F. to 100° F. during the daytime. The individual plants were grown in 10-inch hanging baskets in a soiless medium consisting of Perlite and peat moss. Plants were liquid fed with 20-10-20 plus minor elements. The cutting types were lateral or apical stems. Cuttings were stuck in about the first week of June 2008 and finished in about late October 2008. Light levels were a maximum of 1,000-6,000 ft. candles, depending on cloud cover.

The plant of the present invention has not been observed in all possible environmental and/or cultural conditions. The phenotype may vary significantly with variations in environment such as temperature, light level, humidity and also with cultural practices such as fertility, soil and water quality.

The accompanying photographs illustrate the overall appearance and the flower color of the cultivar of the present invention described herein. The photographs were taken of a mature plant during early inflorescence.

There may be variations between the colors in the photograph and the colors in the following description due to, for example, light reflectance, the amount of blue or red light captured in the film, and/or propagation stress. If such variations occur, then written description shall control.

The following description was taken of the 'CoFlash' cultivar shown in the photographs.

Parentage: The new cultivar was developed by standard cross-pollination. As noted above, its pollen parent was an 'Amazon Sunset' (U.S. Plant Pat. No. 10,864), and the seed parent was 'TiGo' (U.S. Plant Pat. No. 14,118).

Propagation:

*Type of cutting*.—Lateral or apical stems with leaves.

*Time to initiate roots*.—Approximately 12 to 14 days at 70° F. soil temperature, and 70° F. air temperature, with radiant heat applied at the bench top or just below the rooting medium. Winter low light conditions may require longer time to initiate roots.

Appearance and form of mature plant:

*Plant form and habit*.—Plant is free branching and pendulous.

*Plant size*.—Stems generally protrude upwards until they reach about 30 cm. in length, then they become pendulous. Stem length at first flowering is generally about 50 cm. Both of these measurements are a function of age, the above environmental and cultural practices, and can vary accordingly.

*Rooting habit*.—Roots are coarse and somewhat stringy.

*Branching habit*.—Pendulous.

*Stems*.—Habit is pendulous. Internode length on mature stems is about 3 cm. Lateral stems alternate along the main stem. Color does not match any in the chart, but appears between 148B and 148C on all surfaces when juvenile. With age, the surfaces of the stems that are the most exposed to light become densely spotted with a reddish brown color making the color appear close to 177A. The undersurfaces or shaded surfaces tend to remain close to and between 148B and 148C.

*Foliage*.—Shape is linear. Leaves usually numbering 5 or 6 appear in half whorls that alternate in position along the stems.

*Foliage size*.—Size of the largest leaves is about 1.6 cm. in length, and about 2 mm. in width.

*Foliage color*.—Adaxial surface color is closest to 137B and the abaxial surface color is 137C. There is no visible venation. Juvenile foliage adaxial surface color is closest to 137B and the abaxial surface color is 137C. There is no visible venation.

*Foliage texture*.—The foliage texture is smooth with tiny pubescence.

*Petioles*.—There appears not to be any petioles, or if there are any, they are too short to determine, as the leaves appear to be attached directly to the stems.

*Flower habit*.—Outward away from stems.

*Flower size/shape*.—About 1.75 cm. wide and about 3.25 cm. high, and about 0.5 cm. deep. The center petals are fused together appearing as one single petal with each of the fused center petals being about 0.6 cm. Wide and 3 cm. deep, and the shape is linear on one side, and ovate on the other with exaggerated and curved acuminate apex (more like a curved, tapering, acicular or filliform apex), entire margin and cuneate base. Each side petal is about 0.6 cm. wide and about 2.3 cm. long, and the shape is linear on one side, and ovate o the other side, with a cuneate base and acuminate apex, and entire margin. The center petal is about 0.7 cm. wide and about 2.3 cm. long that is strongly reflexed into a u-shape, cuneate base, strongly acuminate apex, and entire margin. These measurements refer to the larger flowers.

*Flower texture*.—Smooth.

*Flower count*.—Usually 3 or 4 flowers per axial.

*Flowers borne*.—Arising from leaf axils, one peduncle per node, with generally one to four pedicels per peduncle, each pedicel producing a single flower. Flowers are single in type.

*Natural flowering season*.—Can be year around under greenhouse conditions, except flowering may decrease or cease during low-light periods of winter, indicating the plant may be somewhat photoperiodic. Little or no vernalization is required and the plants flower continuously when minimum temperatures are below 65° F., except possible photoperiodic responses as stated above. The plant also flowers continuously at sustained minimum temperatures in excess of 65° F., except to a lesser extent. The plants do flower heaviest after about 30 days of minimum temperatures below 50 degrees F.

*Time to flower*.—About 12 weeks from rooted cutting to first inflorescence, depending on the age of the cuttings that were stuck, and other environmental conditions. Budded cuttings flowered earlier than juvenile cuttings.

*Flower shape and color*.—There are 5 petals, with the two largest petals fused together at each side forming a hollow tube-type of single organ that is wider at the base than at the apex. The adaxial surface of each of these petals is close to 17C at the base and the apex appears close to 183A with a small area close to 42A toward the middle of the petal, than another small area close to 45 A toward the base, but each color is hard to determine due to the small size of each area. There are two side petals which parallel the main two fused petals, their adaxial surface is close to 150A at base, then close to 28A from base to midway and apex. There are tiny reddish streaks toward the apex which are very narrow, making the color very hard to determine, but which appear close to 34A and 45A close to the apex. There is a strongly reflexed center petal which attaches to the calyx and covers about half of the abaxial surface of the two side petals, the adaxial surface color is closest to 150C at the base to 34B at about one quarter of the way to the apex. There is a strip between 17C and 17B to about three quarters of the way to the apex with a center strip close to 187B to 187C, to 46 A toward the apex that is in the center of the petal. The abaxial surface of the outer fused petal is close to 20C at the base toward apex, then changing about the middle of the petal to close to 16A. Then about three quarters of the petal toward the apex is a dark strip close to 168A. The apical portion of the petal is colored close to 183A to 183B. The side petals at the base are close to 162B, then a strip of reddish tinged yellow close to 162A to 162B. Most of the remaining portion of the petals toward the apex is closest to 16A. The apex is closest to 16A. The reflexed center petal has about a half centimeter of a base color close to 153C to 153D. Then on each side, is a small spot close to 33A, then there is astrip of close to 17A to 17B on the outer edges that extend from a basal spot of 153C to 153D to about three-quarters of the petal length toward the apex. There is a center strip close to 165A that extends from the basal spot of 153C to 153D to the apex.

*Flower buds*.—Lanceolate in shape, 1 cm. in length and 0.4 cm. in diameter at the base. Bud color prior to opening is close to 143B at the base, and 143B toward the apex with an area of 143C to 143D in the center of the bud.

*Peduncles*.—Length is about 1.3 cm. and diameter is about 1.5 mm. The color does not match any in the chart, but appears between 143B and 143C with extremely tiny reddish spots, which are too small to determine color.

*Pedicels*.—About 0.5 cm. long and about 1 mm. in width. Color is closest to 143B.

*Calyx*.—There is one calyx measuring about 0.5 cm. wide and 1. cm. long. It is sheathing and crown-like in shape with five pointed lobes, each with an acute to acuminate apex. There are two which are longer than the other three. These longer two are curved and follow the curvature of the center reflexed petal described above. The apex of each of the shorter three points is about 0.6 cm. long and the longer two are each about 0.75 cm. long. The adaxial surface is close to 143A at the base, and close to 143A at the apex with a strip close to 143C in the middle.. The abaxial surface is close 143A at the base and 143C at the apex. There is very fine pubescence on both surfaces the color of which cannot be determined due to the tiny size.

*Reproductive organs*.—Ovary is colored 143B to 143C, about 1.25 cm. in length and 1.5 mm. in diameter. The stigma is colored close to 145C, about: 0.1 mm. wide and 2 cm. long. The stamen is a single organ at the base which sheaths the ovary, then it splits into 5 individual filaments, each of which produces a tiny anther that appears close to 153D, but exact color cannot be determined due to the tiny size of the anthers. The stamen and filaments are colored close to 150D. The pollen color appears close to 12C. The pollen is shed before the stigma is receptive to pollen and natural seed production has not occurred.

*Disease resistance*.—Plants seem to be highly resistant or even immune to INSV, TSWV and most other viruses, bacteria and fungi. Plants have been tested in outdoor unscreened conditions where obvious virus contaminations were prevalent and thrip populations were high, but no occurrences of virus contaminations were noticed despite high populations of thrips on the plants in close proximity to plants of other species susceptible to such contaminations, and showing obvious virus symptoms.

*Rooting ability*.—Easy, no hormones needed.

*Cold/heat resistance*.—Plants have flowered continuously under temperatures where maximums exceeded 100° F., and where minimums did not fall below 65° F.

COMPARISON CHART TO PRIOR ART

The major differences of the instant cultivar is compared to 'TiGo'.

| | 'TiGo' | 'CoFlash' |
|---|---|---|
| Stem colors- | 139D | 148B to 148C |
| Foliage surface colors | | |
| Adaxial | 138A | 137B |
| Abaxial | 138B | 137C |
| Flower colors | | |
| Adaxial petal surfaces | | |
| Largest petals - Base | 11C | 17C |
| Apex | 180A to 180B | 183A, 45A, 42A |
| Side petals base | 12A | 150A |
| Midsection | 14A | 28A |
| Apex | 179A, 180A | 34A, 45A |
| Center petal base | 9D | 150C |
| Midsection | 14B | 34B |
| Center strip | 187A to 200A | 17C to 17D and 187B to 187C 46A |
| Abaxial petal surfaces | | |
| Largest petals - base | 31B to 31C | 20C |
| Midsection | 12A | 16A |
| Apex | 171A | 168A and 183A |
| Side petals- base | 37B | 162B |
| Midsection | 13A | 162 A to 162B |
| Apex | 179A | 16A and 29A |
| Center petal - Base | 1C | 153C to 153D |
| Midsection | 179A,164A 163A,166A, 180A | 33A, 17A to 17B 153C to 153D 165A |
| Apex | 175A | 165A |

COLOR CODE CHART

Stems: 139D, 200D

Foliage: 138A, 138B

Flowers: 11C, 180A, 180B, 12A, 14A, 179A, 180A, 14B, 9D, 187A, 200A, 31B, 31C, 171A, 37B, 13A, 179A, 1C, 164A, 163A, 166A, 175A, 145C, 147C Peduncles: 145B, 145C Pedicels: 145B Calyx: 138B, 144B, 144C Reproductive organs: 145A, 153D, 153A, 150C, 11C It is claimed:

1. A new and distinct cultivar of *Lotus* hybrid named 'CoFlash', as illustrated and described herein.

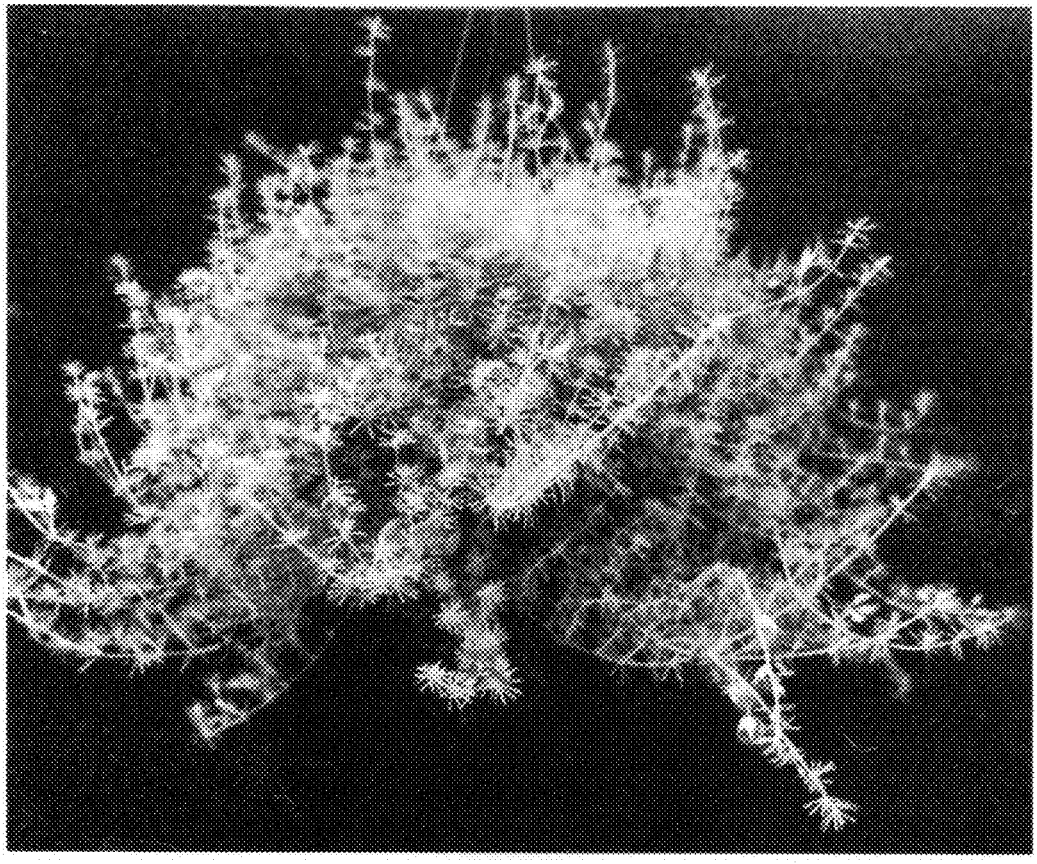

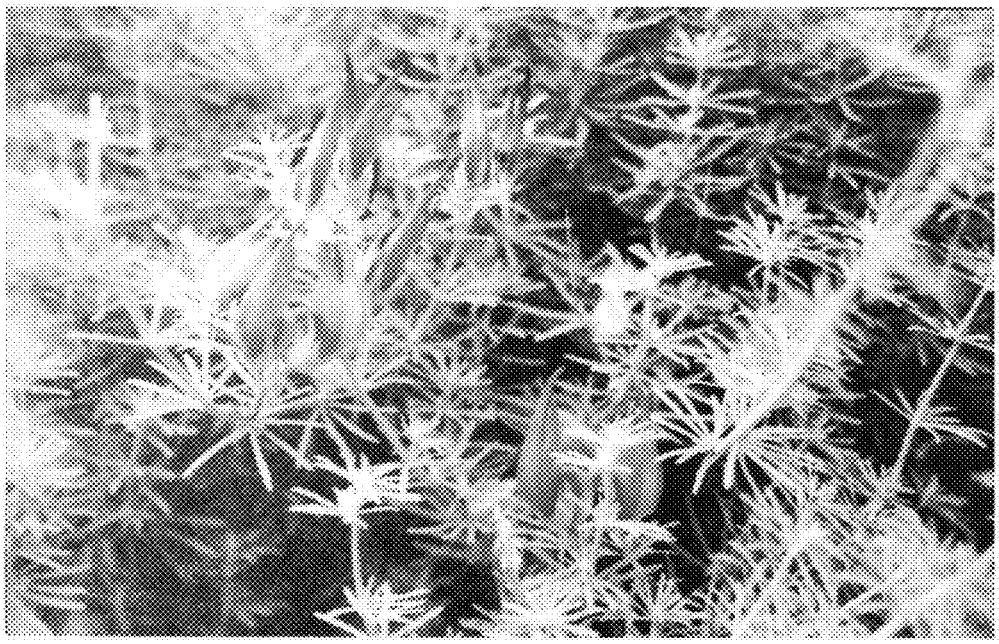

* * * * *